(12) United States Patent
Pohl et al.

(10) Patent No.: US 7,842,511 B1
(45) Date of Patent: Nov. 30, 2010

(54) COLORIMETRIC MONITORING OF REACTIONS IN SOLUTION AND SOLID PHASE AUTOMATED AND MANUAL SYSTEMS

(75) Inventors: Nicola Lucia Pohl, Ames, IA (US); Kwang-Seuk Ko, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1154 days.

(21) Appl. No.: 11/403,381

(22) Filed: Apr. 13, 2006

Related U.S. Application Data

(60) Provisional application No. 60/670,719, filed on Apr. 13, 2005.

(51) Int. Cl.
*G01N 33/00* (2006.01)

(52) U.S. Cl. .................. 436/166; 436/164; 436/800; 422/82.06; 422/82.05

(58) Field of Classification Search ................ 436/166, 436/164, 800; 422/82, 82.085
See application file for complete search history.

(56) References Cited

U.S. PATENT DOCUMENTS

| | | | |
|---|---|---|---|
| 5,512,668 A * | 4/1996 | Stec et al. | 536/25.33 |
| 7,135,565 B2 * | 11/2006 | Dellinger et al. | 536/25.3 |

* cited by examiner

*Primary Examiner*—Sam Siefke
(74) *Attorney, Agent, or Firm*—McKee, Voorhees & Sease, P.L.C.

(57) ABSTRACT

The present invention relates to the a new protecting group, 4-(O-nitrophthalimido)butyric acid (NPB) that may be attached to a monomer unit during oligosaccharide synthesis such that upon cleavage of this molecule, the solution turns orange. The orange color allows the simple colorimetric monitoring of the completion of the cleavage reaction and, upon collection of the colored fraction, quantification of the amount of the monomer unit that was successfully coupled to the solid phase.

10 Claims, 7 Drawing Sheets

*p*-Nitrophenyl carbonate (NPC) as Protecting Group for Carbohydrates

COLORIMETRIC MONITORING OF REACTIONS IN SOLUTION AND SOLID PHASE AUTOMATED AND MANUAL SYSTEMS

CROSS-REFERENCE TO RELATED APPLICATIONS

This application claims priority under 35 U.S.C. §119 of a provisional application Ser. No. 60/670,719 filed Apr. 13, 2005, which application is hereby incorporated by reference in its entirety.

BACKGROUND OF THE INVENTION

Biopolymers, such as nucleic acids, proteins and polysaccharides play important roles in fundamental aspects of cellular functions. These biomolecules are capable of storing as well as transmitting biological information that involves intra- and intercellular events. Unlike polysaccharides, the biological roles and functions of nucleic acids and proteins are relatively well understood and are better appreciated by the scientific community. While nucleic acid and polypeptide-derived natural biopolymers are linear in nature and chemically defined, polysaccharides are structurally more complex. This structural and stereochemical diversity results in a rich content of information in relatively small molecules.

In recent years, efforts are being made towards understanding the biological roles of glycoconjugates (commonly known as glycobiology) in the modulation of protein function, fertilization, chronic inflammation, immune responses and cancer metastasis. It is now well accepted that glycoconjugates present on host cell surfaces provide specific binding sites for the attachment of bacterial and viral pathogens leading to infectious diseases. In addition, it has been demonstrated that the oligosaccharide moieties of several complex glycoconjugates present on tumor cell surfaces have unique structural features. These moieties are attractive targets for developing chemically well-defined, synthetic vaccines for cancer and the design of specific delivery of anticancer drugs on tumor cell surfaces.

The growing appreciation of the key roles of oligosaccharides and glycoconjugates in fundamental life sustaining processes has stimulated a need for access to usable quantities of these materials. Glycoconjugates are difficult to isolate in homogeneous form from living cells since they exist as microheterogeneous mixtures. Further, the purification of these compounds, when possible, is at best tedious and generally provides only very small amounts of the compounds. The difficulties associated with isolation of oligo- and polysaccharides and glycoconjugates from natural sources present a major opportunity for the development and exploitation of chemical synthesis.

The invention of solid phase peptide synthesis dramatically influenced the strategy for the synthesis of these biopolymers. The preparation of structurally defined oligopeptides has benefited greatly from the feasibility of conducting their assembly on various polymer supports. The advantages of solid matrix-based synthesis, in terms of allowing for an excess of reagents to be used and in the facilitation of purification are now well appreciated. However, the level of complexity associated with the synthesis of an oligosaccharide on a polymer support dwarfs that associated with the other two classes of repeating biooligomers. First, the need to differentiate similar functional groups (hydroxyl or amino) in oligosaccharide construction is much greater than the corresponding needs in the synthesis of oligopeptides or oligonucleotides. Furthermore, in these latter two cases, there is no stereoselection associated with construction of the repeating amide or phosphate bonds. In contrast, each glycosidic bond to be fashioned in a growing oligosaccharide ensemble constitutes a new locus of stereogenicity.

The development of protocols for the solid support synthesis of oligosaccharides and glycopeptides requires solutions to several problems. First, the nature of the support material is relevant. The availability of methods for attachment of the carbohydrate from either its "reducing" or "non-reducing" end would be advantageous. Also, selection of a linker which is stable during the synthesis, but can be cleaved easily when appropriate, is critical. A protecting group strategy that allows for high flexibility is desirable. Also important is the matter of stereospecific and high yielding coupling reactions.

Besides synthesis, another major obstacle in the field of glycobiology is monitoring of the synthesis of oligosaccharides and glycoconjugates. Analytical tools for on-bead characterization include High-Resolution Magic Angle Spinning NMR spectroscopy (HRMAS), FT-IR, and Gated-Decoupling $^{13}$C NMR Spectroscopy. While these monitoring methods have been successful, they are not amenable to automated synthesis. Other current methods of monitoring oligosaccharide synthesis include solid state NMR, bead IR, and UV monitoring of cleavage products.

There are currently only five labs in the world that can synthesize complex oligosaccharides. Only one of these labs has successfully automated the process by adapting a conventional peptide synthesizer. To date, none have attempted to design molecules that allow colorimetric monitoring of the process.

In the past, oligonucleotide synthesis in solution has been carried out mainly by the conventional phosphotriester approach that was developed in the 1970s (Reese, C. B., Tetrahedron 1978, 34, 3143-3179; Kaplan, B. E.; Itakura, K. in Synthesis and Applications of DNA and RNA, Narang, S. A., Ed., Academic Press, Orlando, 1987, pp. 9-45). This approach can also be used in solid phase synthesis but coupling reactions are somewhat faster and coupling yields are somewhat greater when phosphoramidite monomers are used. This is why automated solid phase synthesis has been based largely on the use of phosphoramidite building blocks; it is perhaps also why workers requiring relatively large quantities of synthetic oligonucleotides have decided to attempt the scaling-up of phosphoramidite-based solid phase synthesis.

Three main methods, namely the phosphotriester (Reese, *Tetrahedron,* 1978), phosphoramidite (Beaucage, S. L. in Methods in Molecular Biology, Vol. 20, Agrawal, S., Ed., Humana Press, Totowa, 1993, pp 33-61) and H-phosphonate (Froehler, B. C. in Methods in Molecular Biology, Vol. 20, Agrawal, S., Ed., Humana Press, Totowa, 1993, pp 63-80; see also WO94/15946 and Dreef, C. E. in Rec. Tray. Chim. Pays-Bas, 1987, 106, p 512) approaches have proved to be effective for the chemical synthesis of oligonucleotides. While the phosphotriester approach has been used most widely for synthesis in solution, the phosphoramidite and H-phosphonate approaches have been used almost exclusively in solid phase synthesis.

Perhaps the most widely used strategy for the synthesis of oligodeoxyribonucleotides in solution involves a coupling reaction between a protected nucleoside or oligonucleotide 3'-(2-chlorophenyl)phosphate (Chattopadhyaya, J. B.; Reese, C. B. Nucleic Acids Res., 1980, 8, 2039-2054) and a protected nucleoside or oligonucleotide with a free 5'-hydroxy function to give a phosphotriester. A coupling agent such as 1-(mesitylene-2-sulfonyl)-3-nitro-1,2,4-1H-triazole (MSNT) (Reese, C. B.; Titmas, R. C.; Yau, L. Tetrahedron Lett., 1978, 2727-2730) is required. This strategy has also been used in the synthesis of phosphorothioate analogues. Coupling is then effected in the same way between a protected nucleoside or oligonucleotide 3'-S-(2-cyanoethyl or, for example, 4-nitrobenzyl)phosphorothioate (Liu, X.; Reese, C. B. J. Chem. Soc., Perkin Trans. 1, 1995, 1685-1695) and a protected nucleoside or oligonucleotide with a free 5'-hydroxy function.

There is a need in the art for a fast and simple method of colorimetrically monitoring reactions on a solid support for automated chemical synthesis that may be used in addition to other known techniques for monitoring such synthesis.

It is a primary objective of the present invention to provide a novel protecting group to provide colorimetric monitoring for solid and solution phase synthesis.

It is a further objective of the present invention to provide 4-(ortho-nitrophthalimido)butyric acid (NPB) to allow colorimetric monitoring for solid and solution phase synthesis.

It is a further objective of the present invention to provide p-nitrophenyl carbonate (NPC) to allow colorimetric monitoring for solid and solution phase synthesis.

It is a further objective of the present invention to provide a method for assaying to determine the amount and type of a particular chemical produced during solid and solution phase synthesis.

It is yet a further objective of the present invention to provide a method for determining and confirming the presence or amount of a particular chemical produced during solid and solution phase synthesis.

It is another objective of the present invention to provide a kit for determining the presence or amount of a particular chemical produced during solid and solution phase synthesis.

It is still a further objective of the present invention to provide a method of monitoring reactions on solid support for automated synthesis.

It is a further objective of the present invention to provide a method of colorimetric monitoring reactions on solid support for automated synthesis that is simpler and faster than previous techniques.

The method and means of accomplishing each of the above objectives as well as others will become apparent from the detailed description of the invention which follows hereafter.

SUMMARY OF THE INVENTION

The present invention provides a new hydroxyl protecting group, 4-(ortho-nitrophthalimido)butyric acid (NPB), designed and synthesized to allow the first colorimetric monitoring strategy for solid phase and solution phase synthesis of oligosaccharides, oligonucleotides, oligodeoxyribonucleotides, and their analogues. The invention further describes the use of p-nitrophenyl carbonate (NPC) for use in solid and solution phase synthesis. The deprotection of the hydroxyl group for the next coupling cycle produces a colored by-product.

The method of the invention involves attaching the hydroxyl protecting group to a monomer, attaching the monomer to a solid support, placing the hydroxyl protecting group, the monomer, and the solid support in a cleavage solution, and deprotecting the hydroxyl protecting group to cause the formation of a colored by-product. This colorimetric monitoring method is simpler and faster than previously known techniques, including solid state NMR, bead IR, and UV monitoring of cleavage products. The colorimetric monitoring method of this invention can further be used in automated solution phase synthesis, such as fluorous-phase-based systems (see e.g. www.fluorous.com).

DETAILED DESCRIPTION OF THE DRAWINGS

DETAILED DESCRIPTION OF THE PREFERRED EMBODIMENT

In accordance with the present invention, it has been found that a new hydroxyl protecting group is useful in a new strategy for colorimetric monitoring strategy for solid and solution phase synthesis. The strategy lends itself to the synthesis of a variety of different compounds, including oligosaccharides, oligonucleotides, and oligodeoxyribonucleotides. A particularly useful protecting group for this purpose is 4-(ortho-nitrophthalimido)butyric acid (NPB). Another useful protecting group is p-nitrophenyl carbonate (NPC).

The present invention is directed toward a new colorimetric assay method, apparatus and kit specific for the qualitative determination and quantitative estimation of the amount of the monomer unit, such as a fatty acid, monosaccharide, amino acid, or nucleotide, that has been successfully coupled to the solid or solution phase. The method is fast, simple, and effective for quantitatively and qualitatively determining the presence of the monomer unit. The apparatus and kit of the present invention are simple, easy to use, and economical to manufacture. The invention also provides a method of solid or solution phase synthesis of oligosaccharides, oligonucleotides, oligodeoxyribonucleotides, and other compounds, comprising the step of sequentially linking mono- or oligo-groups to a solid support and colorimetric monitoring of the same.

More specifically, the method of the present invention is based upon the deprotection of the hydroxyl group on the monomer by cleavage of the hydroxyl protecting group, NPB or NPC. The deprotection of the hydroxyl group for the coupling cycle in turn produces a colored by-product.

As used herein, the phrase "protecting group" means temporary modification of a potentially reactive functional group which protects it from undesired chemical transformations.

Figure 1:
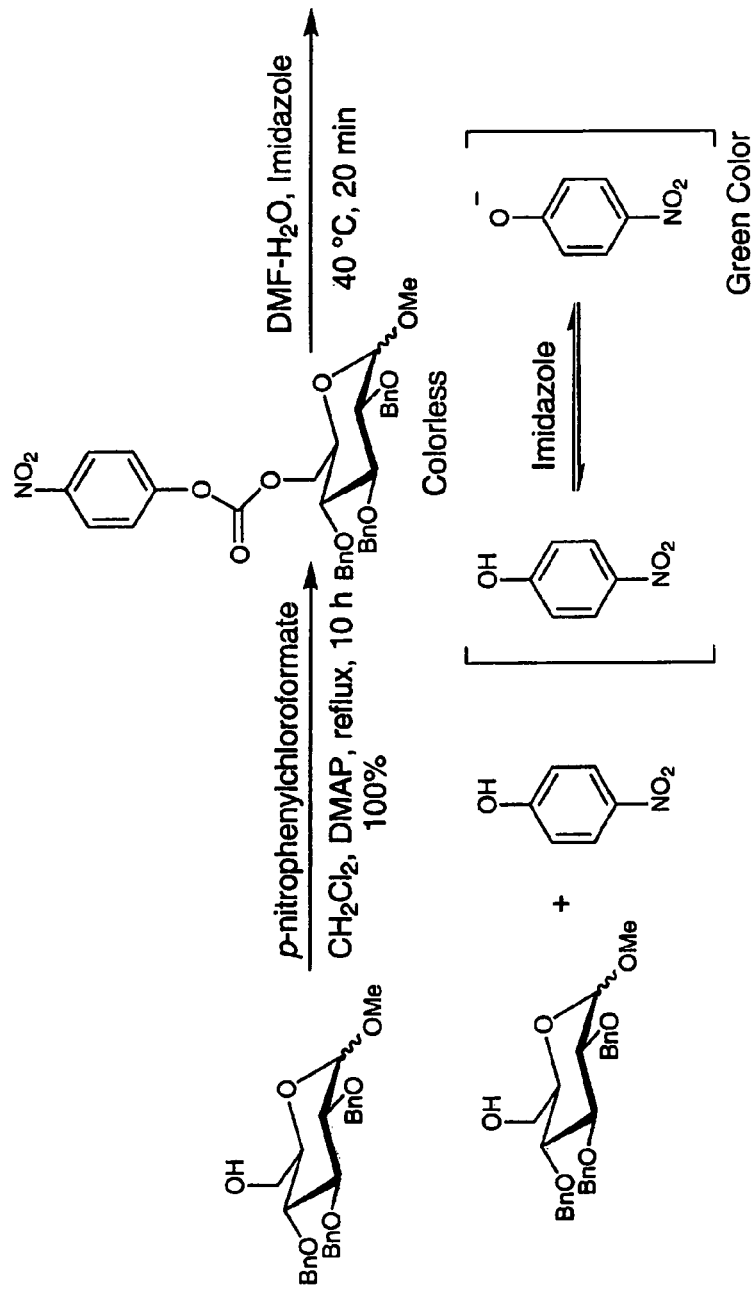
FIG. 1 is a diagram illustrating the use of p-nitrophenyl carbonate (NPC) as a protecting group for carbohydrates.
Figure 2:
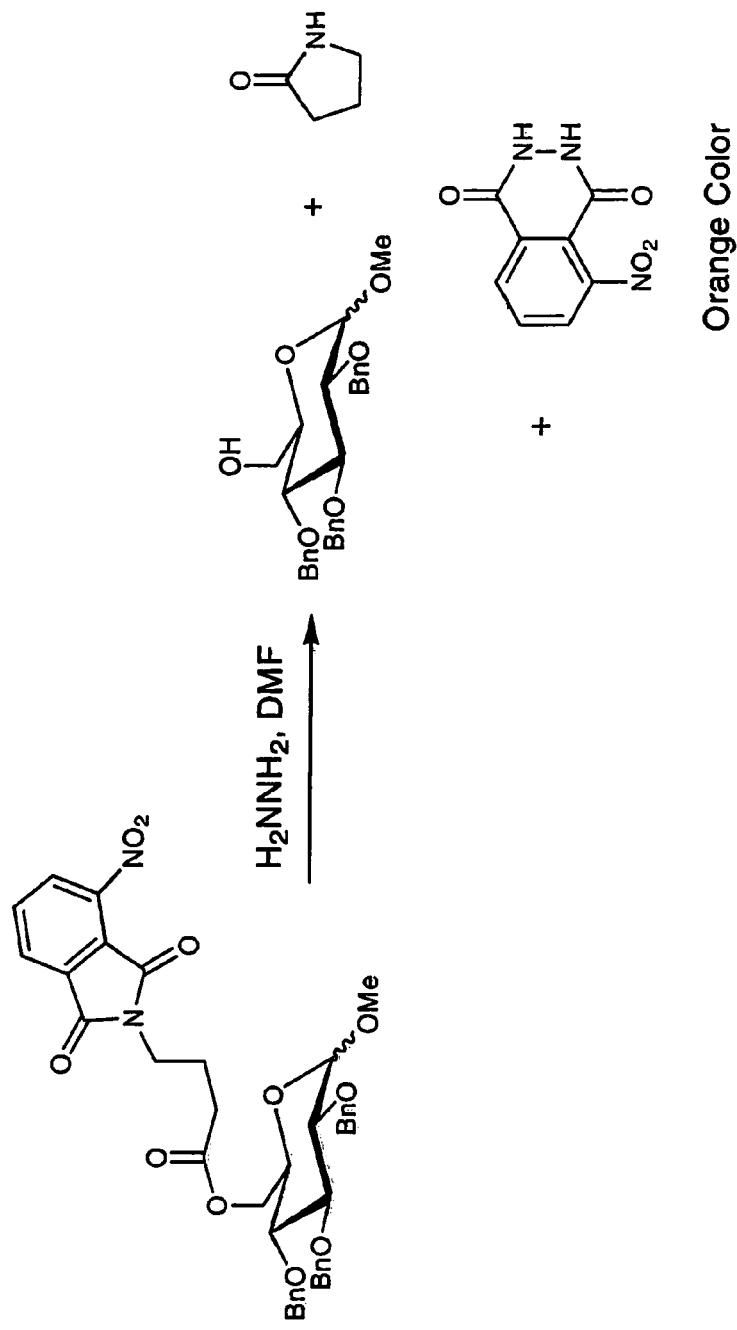
FIG. 2 is a diagram illustrating the novel use of 4-(O-nitrophthalimido)butyric acid (NPB) as a protecting group for carbohydrates.

The novel hydroxyl deprotecting group of this invention is 4-(ortho-nitrophthalimido)butyric acid (NPB). NPB is made by condensation of 4-aminobutyric acid with ortho-nitrophythalic anhydride. The hydroxyl protecting group is stable to oxidation and strong anhydrous acids and is easily removed by basic aqueous hydrolysis or buffered hydrazine. The invention also relates to the novel use of p-nitrophenyl carbonate (NPC) as a protecting group for the same purpose. FIGS. 1 and 2 illustrate examples of schemes for the use of NPC and NPB as protecting group for carbohydrates, respectively.

Figure 3:
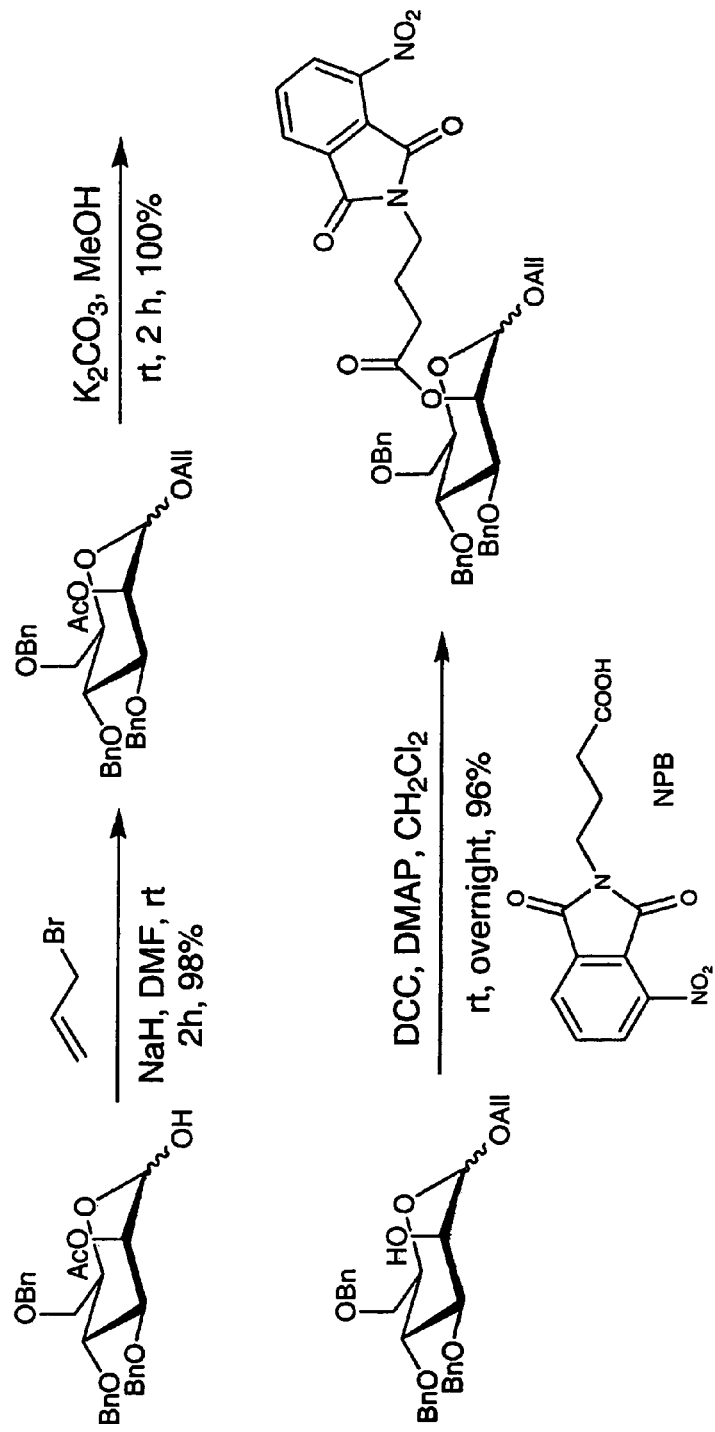
FIG. 3 is a diagram illustrating the synthesis of NPB-protected mannose building block.
Figure 4:
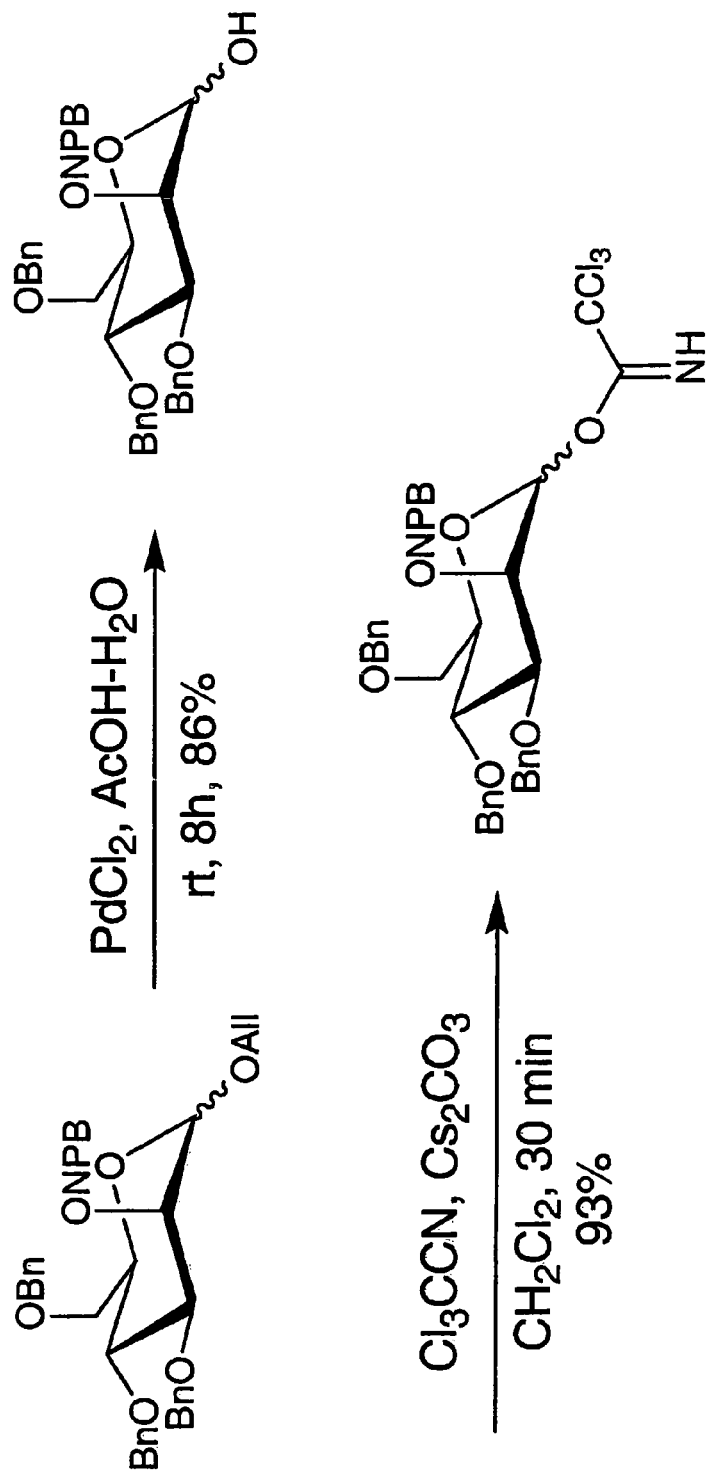
FIG. 4 is a diagram illustrating the conversion of NPB-protected building block into the trichloroacetimidate.

The NPB or NPC is generally attached to the monomer unit. The NPB group can be converted to the acid chloride and then reacted with the alcohol to be protected in the presence of a base or a direct coupling of the acid by standard techniques such as carbodiimide couplings. FIG. 3 is a diagram showing the synthesis of NPB-protecting mannose building block which illustrates a preferred means and monomer to which the NPB may be attached. FIG. 4 shows trichloroacetimidate conversion as a standard method for activating the sugar to couple to the sugar on the solid support.

Figure 5:
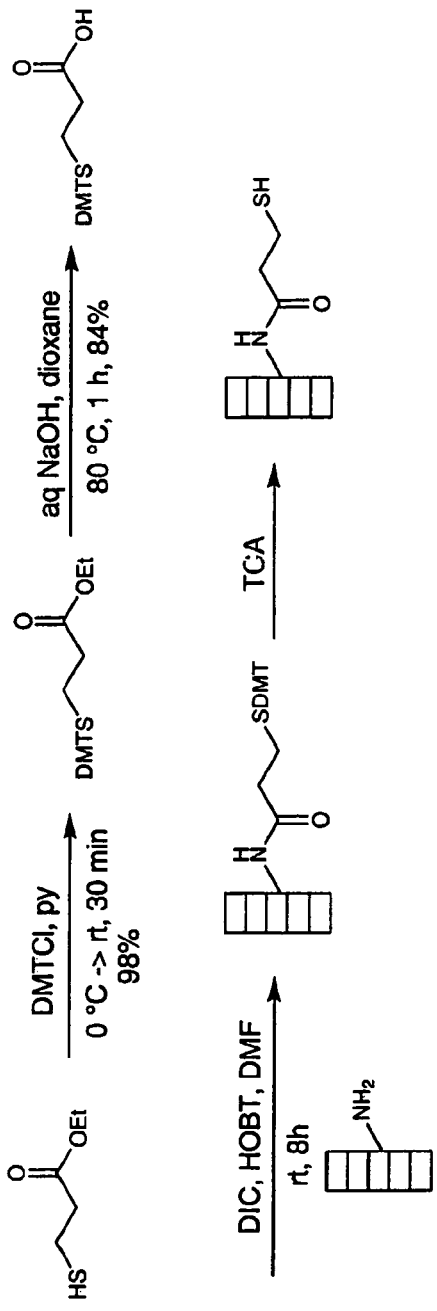
FIG. 5 is a diagram illustrating the synthesis of thiol linker using lantern solid support.

The connection of the NPB-protected monomer to the solid support is accomplished through a linker which can be viewed as a support-bound protecting group. A variety of linkers have previously been prepared for the attachment of hydroxyl groups to the solid phase. Linkers for solid and solution support synthesis are well known in the art and include, but are not limited to, silyl ethers, thioethers, succinyl esters and nitrobenzyl ethers. Such linkers are well known in the art. A preferred linker for use in this invention is a thiol linker, the synthesis of which is shown in FIG. 5.

The monomer unit of the present invention can be immobilized on a variety of solid or soluble supports including, but not limited to, polystyrene, polyethylene, Teflon, silicon gel beads, hydrophobized silica, mica, filter paper (e.g. nylon, cellulose, and nitrocellulose), glass beads and slides, gold and all separation media such as silica gel, sephadex, and other chromatographic media. These and other such supports are well known in the art.

Monomers appropriate for use in the invention are those having a free hydroxyl group. Examples of such monomers include, but are not limited to, carbohydrates that may be glycosides, aminoglycosides, or ether- or amino-linked sugars, where the coupling takes place through a non-glycosidic position. The building block mono- or oligosaccharide-donors may be any activated sugar including, but not limited to, orthoesters, thioorthoesters, cyanoalkylidene derivatives, 1-O-acyl sugars, amino sugars, acetimidates, trichloroacetimidates, thioglycosides, aminoglycosides, amino-oligosaccharides, glycosylamines of oligosaccharides, glycosyl thiocyanates, pentenyl glycosides, pentenoylglycosides, isoprenyl glycosides, glycals, tetramethylphosphoro diamidates, sugar diazirines, selenoglycosides, phosphorodithioates, glycosyl-dialkylphosphites, glycosylsulphoxides and glycosylfluorides. The individual saccharide residues are attached directly to the linkers via their anomeric carbons, and the linkers have the characteristic that at least one set of conditions for releasing the saccharides, oligosaccharides, and/or polysaccharides from the solid support provides saccharides, oligosaccharides, and/or polysaccharides wherein the residues that were attached directly to the solid support are transformed into glycosyl donors. In one embodiment of this invention, the molecule is mannose, which may be used in the synthesis of polymannoses, such as dimmanopyranoside.

One or more of the molecules to be coupled may be tagged such as, for example, a fluorous-tagged molecule. The procedure for tagging molecules having protecting groups is well known in the art. The conditions will vary depending upon the tag(s) chosen, substrate used, etc. An exemplary and well known reference in this respect is T. W. Green, P. G. M. Wuts, *Protective Groups in Organic Synthesis*, Wiley-Interscience, New York, 1999, the contents of which are specifically incorporated herein by reference. This book provides detailed information to persons skilled in the art regarding the tagging conditions/procedures to use depending on the protecting group selected.

Following coupling of a monomer unit, such as a protected monosaccharide, to the solid or solution-based support, the NPB or NPC group can be removed using buffered hydrazine to form an orange colored by-product. More specifically, the hydrazine binds to the protecting group to reveal the free hydroxyl group, which in turn causes the formation of the orange color. Appropriate types of hydrazine for this purpose include, but are not limited to, hydrazine acetate, hydrazine sulfate, and hydrazine hydrate.

Once the monomer, oligomer or polymer is tethered to the solid support, the molecule is deprotected, thereby liberating the hydroxyl protecting group. This deprotection, in turn, causes the cleavage solution to turn orange. The cleavage solution is aqueous and includes hydrazine.

Figure 6:
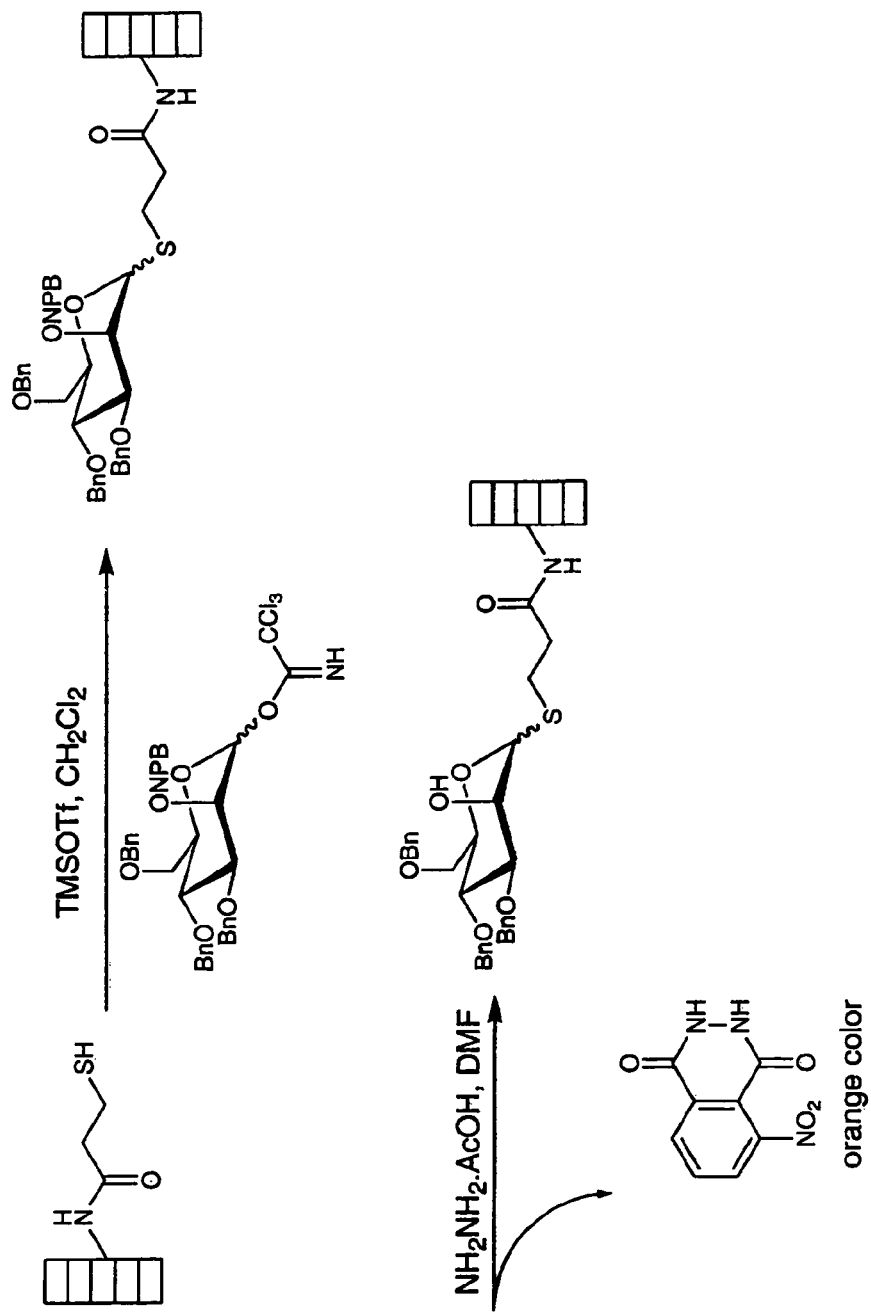
FIG. 6 is a diagram illustrating solid-phase synthesis of oligosaccharides.
Figure 7:
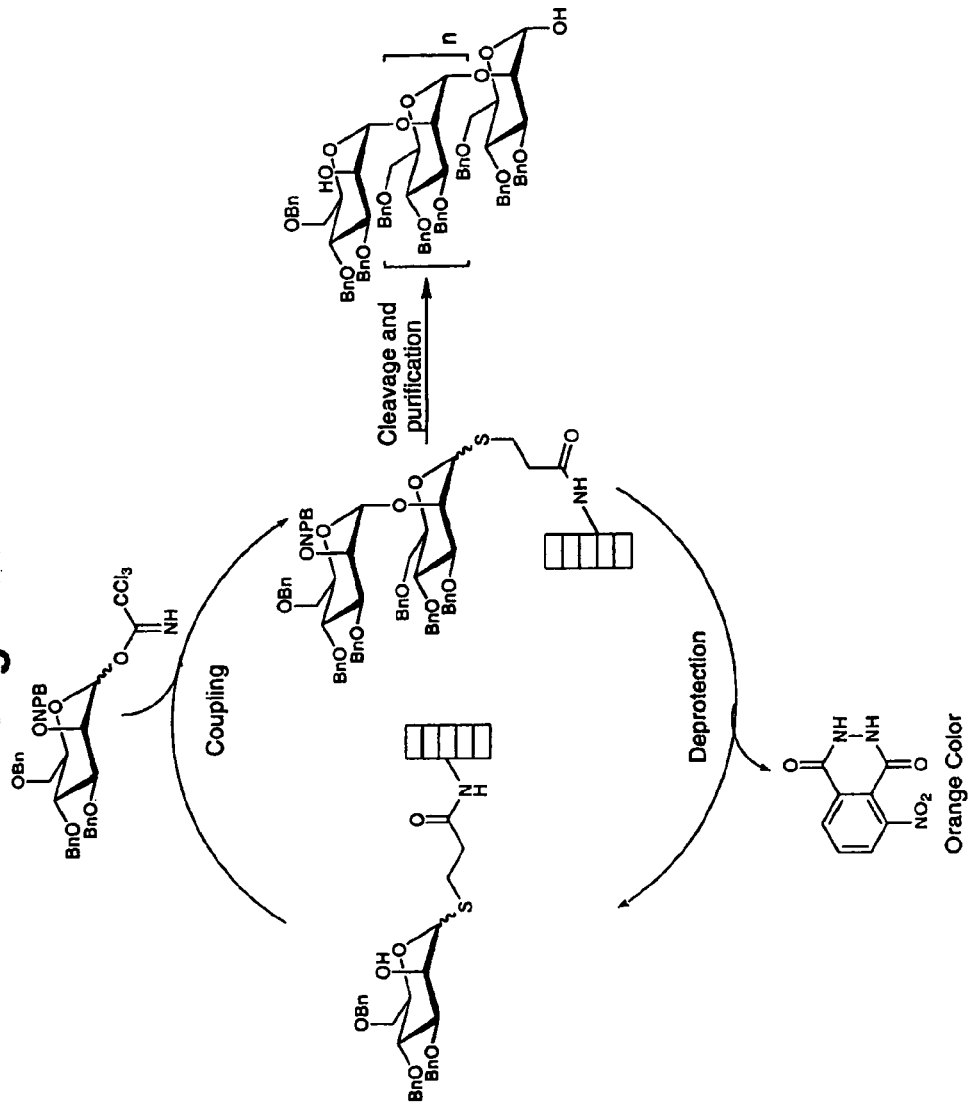
FIG. 7 is a diagram illustrating new solid-phase synthesis strategy for oligosaccharides.

The synthesis of oligosaccharides, oligonucleotides, etc. on the solid or soluble support requires the development of a coupling cycle which consists of a series of operations required to elongate the growing chain by one unit. An example of a coupling cycle envisioned for use in this invention is illustrated in FIGS. 6 and 7. Attachment of an appropriately protected monomer through its reducing end is followed by removal of the hydroxyl protecting group from a uniquely designated hydroxyl group. Washing steps to clean the support follow. The exposed hydroxyl group functions as a glycosyl acceptor during the coupling step by reaction with the glycosyl phosphate glycosyl donor (3-4 equivalents) in the presence of an acid, such as trimethylsilyltriflate or boron trifluoride etherate as an activator. After several washing steps any unreacted glycosyl acceptor hydroxyl groups are capped off by reaction with acetic anhydride to prevent the formation of deletion sequences by reaction of these sites during subsequent coupling cycles. Repetition of this cycle will lead to the formation of compounds containing β-glycosidic linkages. Cleavage from the solid support and final deprotection followed by purification are expected to yield the desired oligosaccharide product.

The coupling cycle outlined above consists of a series of relatively simple steps which lend themselves for automation. All other operations would be similar to operations carried out on automated oligonucleotide or oligopeptide synthesizers.

The orange color resulting from the deprotection of the hydroxyl group allows the simple colorimetric monitoring of the completion of the cleavage reaction and, upon collection of the colored fractions, quantification of the amount of the monomer unit that was successfully coupled to the solid phase.

The colorimetric change resulting from deprotection of the monomer can be detected using many methods. In preferred embodiments of the present invention, a color shift may be observed simply by visual observation. In other instances, spectral test equipment well known in the art is employed to detect changes in spectral qualities beyond the limit of simple visual observation, including optical density to a particular illuminating light wavelight. For example, using a spectrometer, the spectrum of the material may be measured before and after deprotection, and the colorimetric response (% CR) may be measured.

For the above-stated reasons, it is submitted that the present invention accomplishes at least all of its stated objectives.

Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components to and steps in any sequence which is effective to meet the objectives there intended.

What is claimed is:

1. A method of colorimetric monitoring of deprotection cycles of reactive functional groups of monomers, comprising:
    attaching a hydroxyl protecting group selected from the group consisting of 4-(ortho-nitrophthalimido)butyric acid and p-nitrophenyl carbonate to a monomer;
    attaching the monomer to a support;
    placing the hydroxyl protecting group, the monomer, and the support in a cleavage solution; and
    deprotecting the hydroxyl protecting group to cause the formation of a colored by-product, which, by measuring its color, monitors the completeness of the deprotection reaction.

2. The method of claim 1 whereby the monomer has a free hydroxyl group.

3. The method of claim 1 whereby the monomer is a carbohydrate.

4. The method of claim 1 whereby the by-product is colored orange.

5. The method of claim 1 whereby the cleavage solution comprises hydrazine.

6. The method of claim 1 whereby the support is a solid support.

7. The method of claim 1 whereby the support is a soluble support.

8. The method of claim 1 that is automated.

9. The method of claim 1 that includes several cycles.

10. The method of claim 5 whereby the cleavage solution is selected from the group consisting of hydrazine acetate, hydrazine sulfate, and hydrazine hydrate.

* * * * *